United States Patent [19]

Madanshetty

[11] Patent Number: 5,594,165
[45] Date of Patent: Jan. 14, 1997

[54] METHOD AND APPARATUS FOR DETECTION OF PARTICLES IN ULTRA-PURE LIQUIDS USING ACOUSTIC SCATTERING AND CAVITATION

[75] Inventor: Sameer I. Madanshetty, Cambridge, Mass.

[73] Assignee: Trustees of Boston, Boston, Mass.

[21] Appl. No.: 621,511

[22] Filed: Mar. 25, 1996

Related U.S. Application Data

[63] Continuation of Ser. No. 257,416, Jun. 7, 1994, abandoned.
[51] Int. Cl.[6] .................................................. G01N 15/06
[52] U.S. Cl. ............................................ 73/61.75; 73/64.53
[58] Field of Search ................................. 73/61.42, 61.53, 73/61.75, 61.79, 61.71, 64.53

[56] References Cited

U.S. PATENT DOCUMENTS

| | | | |
|---|---|---|---|
| 3,538,747 | 1/1968 | Munch | 73/53 |
| 3,608,715 | 9/1971 | Snyder et al. | 73/52 |
| 3,614,069 | 9/1971 | Murry | 259/1 |
| 4,112,735 | 9/1978 | McKnight | 73/19 |
| 4,130,010 | 12/1978 | Wonn | 73/19 |
| 4,689,986 | 9/1987 | Carson et al. | 73/19 |
| 5,219,401 | 6/1995 | Cathignol et al. | 128/660.03 |

FOREIGN PATENT DOCUMENTS

| | | | |
|---|---|---|---|
| 725014 | 3/1980 | U.S.S.R. | G01N 29/02 |

*Primary Examiner*—Hezron E. Williams
*Assistant Examiner*—Jay L. Politzer
*Attorney, Agent, or Firm*—Baker & Botts, L.L.P.

[57] ABSTRACT

A method of detecting particles in ultra-clean liquids using acoustic scattering and cavitation comprises inducing gas caps to form on the particles. The gas caps are then separated from the particles to form bubbles in the liquid. An acoustic signature received as an echo from the bubbles is detected. The detection of the acoustic signature indicates the presence of particles in the liquid.

23 Claims, 4 Drawing Sheets

METHOD AND APPARATUS FOR DETECTION OF PARTICLES IN ULTRA-PURE LIQUIDS USING ACOUSTIC SCATTERING AND CAVITATION

This application is a continuation of application Ser. No. 08/257,416, filed Jun. 7, 1994, now abandoned.

BACKGROUND OF THE INVENTION

1. Field of the Invention

This invention relates to the field of detection of particles in liquid, and particularly to the detection of particles in ultra-pure liquids. More particularly this invention relates to the detection of submicron particles in ultra-pure liquids.

2. Description of the Related Art

Many fields utilize liquids whose purity is critical. For example, in the nuclear power industry, water is used in a nuclear reactor in the nuclear power generation process. Purity of this water is of utmost criticality to ensure the safe and effective operation of the nuclear reactor. Liquids used in silicon chip manufacture are also preferably ultra-pure. Certain other liquid chemicals are manufactured to be ultra-pure for various other applications.

Generally, after distillation, filtration and treatment for organic and ionic removal, liquids required to be ultra-pure may be tested for purity. In practice, however, ultra-pure liquids are generally only tested for ionic content using well known ionic content detection methods. Particulate purity, on the other hand, is more difficult to accurately test. Many times the particulate purity of the liquid is simply assumed by relying upon the integrity of the filtration process.

Optical techniques such as those employing optical scattering and the use of optical microscopes have been used in an attempt to test the particulate purity of a liquid. Optical techniques, however, are ineffective if the liquid medium is colored or if the access to the liquid is not transparent. In many applications, the liquids are stored in metal containers or pipes, so testing using optical techniques entails removal of at least a portion of the liquid to a transparent vessel. In applications such as the nuclear power plant, removal of the reactor water generally requires a shut down of the nuclear reactor and thus the entire power plant. Shutting down to test for particulate purity in the reactor water on a regular basis is impractical and therefore, the optical technique is unworkable in this and many other environments.

Electron microscopy techniques have also been employed. Like optical techniques, however, this method requires the removal of a sample for placement in the viewing area of the microscope. Further, in electron microscopy, a vacuum environment is required. This technique may also be unworkable in many environments. Laser techniques have also been attempted but are generally ineffective in opaque media.

Attempts to use acoustic scattering have also been made. Acoustic scattering involves the detection of acoustic waves echoed off of bodies embedded in a three-dimensional, infinitely propagating media when presented with an acoustic signal. Differing shaped and sized bodies produce differing acoustic waves. The acoustic waves received, or echoed back, are referred to as an acoustic signature for the particular size and shape of the body in the media. Acoustic scattering as a method for testing the particulate purity of liquids, however, has generally been ineffective because the acoustic signature of liquid borne particles, especially submicron particles, is very weak and difficult to detect.

SUMMARY OF THE INVENTION

Therefore, a need has arisen for a method and apparatus to effectively detect particles in liquids, particularly ultra-pure liquids. Further, a need has arisen for a method and apparatus to enhance the acoustic scattering signature of a particle to allow for utilization of acoustic scattering techniques for particulate purity testing.

Accordingly, it is an object of the present invention to provide a method and apparatus to detect the presence of particles in liquids, especially liquids which are required to be ultra-pure.

It is another object of the present invention to provide a method and apparatus for particulate purity testing which is effective for use in transparent or opaque liquids.

It is a further object of the present invention to provide a method and apparatus for particulate purity testing which is in-line and thus does not require the removal of a sample for examination.

It is yet another object of the present invention to provide a method and apparatus for particulate purity testing which does not require the use of vacuum for sample examination.

It is another object of the present invention to provide a method and apparatus for using acoustic scattering techniques for particulate purity testing.

It is still a further object of the present invention to provide a method and device for producing cavitation for in-line acoustic scattering detection of particles.

Various embodiments of the present invention are provided. One preferred embodiment comprises a method of detecting particles in ultra-clean liquids using acoustic scattering and cavitation. First, gas caps are induced on the particles. The gas caps are then separated from the particles to form bubbles in the liquid. An acoustic signature received as an echo from the bubbles is detected. Detection of the acoustic signature indicates the presence of particles in the liquid.

In one embodiment of the present invention, gas cap formation is caused by the use of an active transducer generating a high frequency acoustic signal. Further, separation of the gas caps from the particles is provided by the use of a cavitation field generated by a low frequency, high pressure acoustic signal. In another embodiment, the high frequency acoustic signal and the low frequency, high pressure acoustic signal are confocused.

One technical advantage of the present invention comprises the in-line detection of particles in a liquid.

Other objects and advantages of the present invention will be apparent when the preferred embodiments of the present invention and the drawings are considered.

DETAILED DESCRIPTION OF THE PREFERRED EMBODIMENTS

Figure 1:
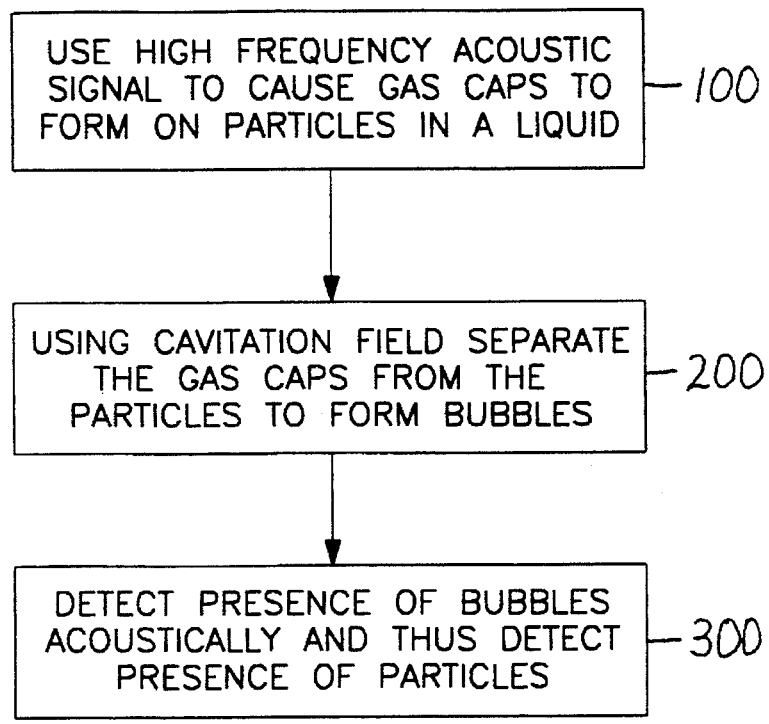
FIG. 1 depicts a flow diagram of a method according to the present invention.

Referring to FIG. 1, one embodiment of the present invention is depicted in a flow diagram. The present invention comprises a method of generating a high frequency acoustic signal which induces gas caps to form on particles in a liquid (100). An active transducer which produces a 30 MHz, 0.5 bar peak negative focused acoustic signal may be used to generate the high frequency signal. Next, particles having gas caps formed thereon are passed through a cavitation field to separate the gas caps from the particles and form bubbles in the liquid (200). A cavitation transducer, such as one which produces a 0.75 MHz, 15 bar peak negative focused acoustic signal may be used to generate the cavitation field. Then, echoes received as a result of acoustic signals being reflected off of the bubbles may be detected (300). Either the active transducer or a passive transducer may be used for detection.

The present invention utilizes cavitation to enhance the acoustic signal of particles in liquids which are required to be ultra-pure in order to effectively use acoustic scattering for particle detection. Clean liquids do not cavitate easily. A pure liquid purged of all particulate impurities and stored in a perfectly smooth container can attain its theoretical tensile strength before undergoing cavitation or fracture. Under ideal conditions, water can be as strong as aluminum; tensile strength of water based on the homogeneous nucleation theory exceeds 1000 bars. In cavitation studies tensile strengths of liquids are often quoted in terms of negative pressures. Further, threshold is understood as the pressure amplitude at which the first occurrence of cavitation is detected. Observed strengths (thresholds) of these clean liquids in practice, however, are generally much lower than the theoretically possible strengths described above. Rarely does the strength of even a reasonably clean liquid exceed a few bars, primarily because gas pockets exist within liquids which provide the necessary seeding for cavitation. A gas pocket is often stabilized in a crevice, either in the container wall or on a liquid-borne particle. In free-flowing pipes, few crevices exist other than particles in the liquid. Therefore, the cavitation which may be induced in the liquid is directly proportional to the quantity of particles present in the liquid. Thus, by inducing cavitation in a liquid and then using acoustic scattering to detect the ensuing transient bubble activity, the presence and quantity of particles in the liquid may be detected.

Cavitation may occur if a sound wave imposes sufficiently strong tensile fields. The oscillating pressures created by the sound wave place restrictions on the time duration of the available tensile field. At high frequencies it becomes increasingly difficult to bring about cavitation because insufficient time is available for bubble growth, which precedes the cavitational implosion. Consequently, the cavitation thresholds of bubbles become greater at higher frequencies and for practical purposes it becomes very difficult to bring about cavitation (in water) at frequencies in excess of 3 MHz. The present invention thus utilizes a high frequency signal to lower the threshold of the liquid and then uses a lower frequency signal to cause cavitation.

Acoustic cavitation has been extensively discussed in "Physics of Acoustic Cavitation in Liquids," *Physical Acoustics,* Flynn, H. G., 1st Ed. 1964, pp. 57–172, "Acoustic Cavitation," *Phys. Rep.,* Neppira, E. A., 1980, pp. 160–251, "Acoustic Cavitation," *Methods of Experimental Physics,* Apfel, R. E., 1981, pp. 355–411, and "Physics of Acoustic Cavitation," *Frontiers in Physical Acoustics, XCIII,* Prosperetti, A., 1986, p. 145–188. For a more concise understanding of cavitation, consider a free bubble in the path of a sound wave. The bubble expands and contracts in response to the pressure alterations of the sound wave; the energy stored during the expansion being returned concentrated during the possibly implosive collapse. Should a bubble grow to two and a half times its original size during the negative excursion of the acoustic pressure then during the following positive half cycle its speed of collapse may become supersonic. Such almost single cycle violent events are called transient cavitation.

Unlike the dramatic bubble growth within a single acoustic cycle as seen in transient cavitation, there exists a more gradual process, termed rectified diffusion. Under favorable conditions, a small bubble exposed to a continuous sound wave tends to grow in size if rectified diffusion is dominant. According to Henry's law, for a gas soluble in liquid, the equilibrium concentration of the dissolved gas in the liquid is directly proportional to the partial pressure of the gas above the liquid surface, the constant of proportionality being a function of temperature only. When a bubble expands, the pressure in the bubble interior falls and gas diffuses into the bubble from the surrounding liquid. When the bubble contracts, the pressure in the interior increases and the gas diffuses into solution in the surrounding liquid. However, the area available for diffusion is larger in the expansion mode than in the contraction mode and consequently there is a net diffusion of the gas into the bubble from the surrounding liquid over a complete cycle. In this manner bubbles grow due to rectified diffusion.

However, a bubble can grow only up to a critical size—the resonance radius determined by the frequency of the impressed sound wave. For small amplitude oscillations a bubble acts like a simple linear oscillator of mass equal to the virtual mass of the pulsating sphere, which is three times the mass of displaced fluid, and stiffness primarily given by the internal pressure of the bubble. Surface tension effects are significant for small bubbles. Ignoring surface tension there is a simple relation for the resonance radius of air bubbles in water:

$$(\text{Resonance radius in } \mu\text{m})\times(\text{insonification frequency in MHz})=3.2$$

This relation is valid to within 5% even for bubbles of radius 10 μm. The bubble response becomes increasingly vigorous at resonance radius, and is limited by the damping mechanisms in the bubble environment—viscous damping, acoustic radiation damping and thermal damping. A post-resonance bubble may exhibit nonlinear modes of oscillations or become transient if the forcing acoustic pressure amplitude is adequately high.

In step 100, a high frequency acoustic signal is used to induce the formation of pockets of gas on the particle. These pockets of gas are referred to as gas caps. Gas cap formation is made possible by the existence of very small gas dots on the surface of the particles. Solids, such as particles, disposed in liquid have at least microscopic surface areas which do not become wetted. Very few solids have geometrically smooth surfaces. Solids in a glass state may have smooth surfaces. Also carefully cleaved crystal surfaces may be smooth initially. From a practical point of view, the notion of smoothness for real surfaces implies that roughness below a certain length scale be ignored. If even fine length scale matters are considered, then roughness must persist at some level. Adsorption studies on various powder surfaces have revealed the presence of fractual surfaces even to the molecular levels. At some scale of fineness there must be unwet sites on the solid surface. This roughness is assumed to be below 500 Å because the measurements of the polystyrene used in the first example discussed below under an electron microscope revealed no such fractures. Wetting does not occur on the entire solid surface because no solid has a geometrically smooth surface when viewed at the microscopic level. Because liquids operate to minimize surface energy which minimizes free surfaces, these microscopic areas of roughness trap gas therein and thus do not become wetted with liquid. These areas of roughness, however, are microscopic and believed to be at the nanometer length scale. Gas trapped in the areas of roughness are thus referred to as nano-gas-dots. Nano-gas-dots may comprise gas released in the dissolved state, vapor molecules from the host liquid, and, under favorable circumstances, desorption of absorbed non-polar constituents.

Figure 2A:
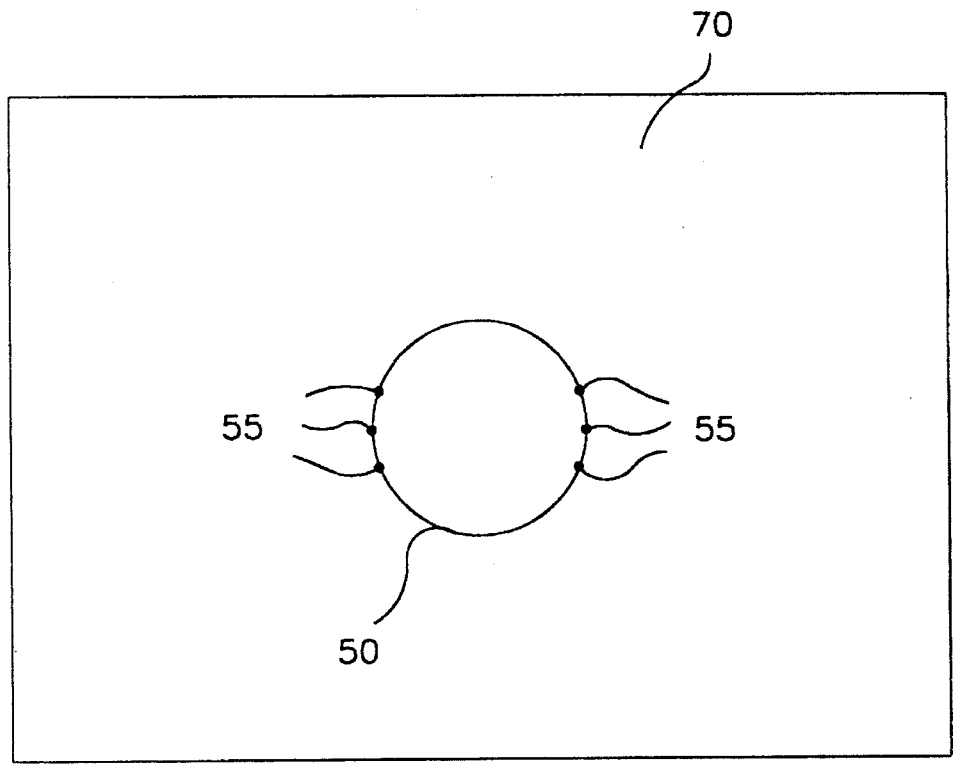
FIG. 2(a) depicts a schematic representation of a particle in a liquid having nano-gas-dots disposed thereon.

Referring to FIG. 2(a), a particle 50 in a liquid 70 is depicted as having a plurality of nano-gas-dots 55 disposed thereon. As discussed above, the size of nano-gas-dots 55 is very small and thus the depiction in FIG. 2(a) is disproportionate only for purposes of illustration.

When a sound wave, such as that generated by the high frequency acoustic signal, is introduced into the liquid, all of the contents of the liquid oscillate in response, assuming the frequency of the sound wave is high enough to make the thickness of the vorticity boundary layer small. A component of the liquid which is heavier than the liquid oscillates with an amplitude less than that of the liquid. A component which is lighter than its surrounding liquid oscillates with a greater amplitude than that of the liquid.

In general, the density of particle 50 does not differ significantly from that of liquid 70, and consequently particle 50 follows the oscillation path of liquid 70. Generally, nano-gas-dots 55 on the surface of particle 50, however, have an amplitude of oscillation of almost three times that of liquid 70. This difference in amplitude of oscillation is significant because nano-gas-dots at this amplitude may bridge with a neighboring dot due to the attraction forces between them. For example, two pulsating hemispherical nano-gas-dots closely separated by 50 nanometers on a plane such as a particle surface having a one micron diameter spherical shape, may coalesce as a result of mutual attraction.

Figure 2B:
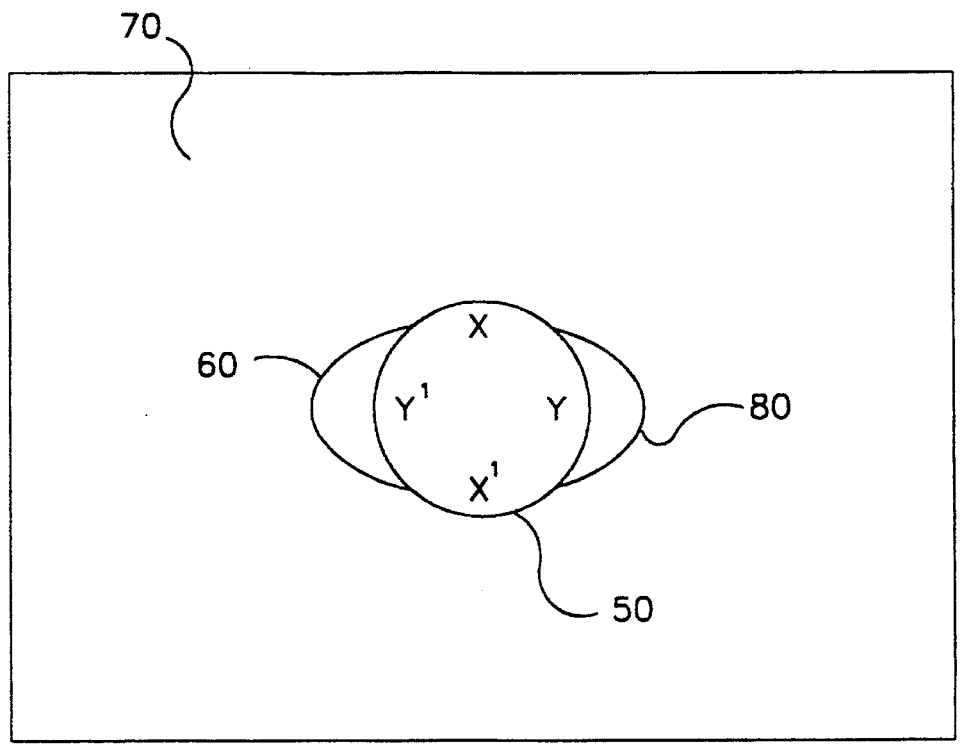
FIG. 2(b) depicts a schematic representation of a particle in a liquid during formation of gas caps on the particle.

Referring to FIG. 2(b), the effect of the high frequency acoustic signal on particle 50 and nano-gas-dots 55 is depicted. Nano-gas-dots 55 on the surface of particle 50 are attracted to one another when they are accelerated due to oscillation generated by the sound waves and tend to accumulate to form gas caps 60, 80 disposed at the poles along the axis of oscillation opposite on particle 50 as depicted in FIG. 2(b). Gas caps 60, 80 may also be enlarged when particle 50 accelerates through liquid 70 due to the sound wave pressure exerted thereto. When high accelerations due to the sound waves occur, liquid tends to become supersaturated with dissolved gas and therefore, this dissolved gas may be transferred into gas caps 60, 80. Gas caps 60, 80 tend to be crescent shaped due to the tensile field around the particle. Gas caps 60, 80 may also be partially vaporous even though nano-gas-dots 55 are unlikely to contain significant amounts of vapor. Gas caps 60, 80 maintains contact with particle 50 due to surface tension. This surface tension is generally strong enough to maintain contact with gas caps 60, 80 up to a critical gas cap size.

Gas cap linking as at Y and Y' in FIG. 2(b) and gas cap distortion and possible non uniform enlargement may occur as at X and X'. Further, two pulsating hemispherical nano-gas-dots closely separated on a plane-more specifically, closely separated 50 nm gas dots on a one micron diameter sphere surface-may coalesce as a result of a mutual attraction (for favorable conditions at the contact line, possibility of slipping or appropriately receding contact angle). This will progressively enlarge the gas caps.

Additionally, at Y, as the particle accelerates to the right as in FIG. 2(b), the liquid in proximity should appear supersaturated (with dissolved gas) as a consequence of high accelerations, and may facilitate transfer of gas into the gas cap. When the acceleration reverses, the gas cap developed at Y tends to be squashed, flattened out against the barrier posed by the sphere surface, thus enlarging the area of the gas cap film on the particle. The gas cap rotates to X because of the squashing at Y is free to oscillate to and fro on the top of the sphere. In the case of a nano-gas-dot mid way between X and Y (or, say at 30° latitude in FIG. 2(b)), during acceleration, it moves towards Y. The same nano-gas-dot in the reversed acceleration phase encounters a material barrier due to the spherical particle that resists the body force of the kinetic buoyancy. Under these circumstances, the nano-gas-dot may be thought to be experiencing a rectified kinetic buoyancy, which promotes the agglomeration of nano-gas-dots. If a significant gas cap were to develop at Y, the particle may rotate under the unbalanced radiation torque so that Y takes up the position at X or X'. The largest gas caps tend to form at X and X' where the poles along the axis of oscillation exist. The tensile field around the particle ensures that the gas cap is crescent shaped; excess pressure for spherical surface formation in the presence of surface tension is provided by the tensile environment.

At a particular frequency of sound wave used, the speed at which gas caps form on particle 50 is directly related to the size of the particle due to viscosity effects. Every particle has a characteristic frequency. For example, for a particle having a diameter of 0.984 µm, 0.481 µm, and 0.245 µm, the characteristic frequency is 2.16 MHz, 9 MHz and 34 MHz, respectively. If the frequency of the sound wave used is greater than the characteristic frequency of the particle, gas cap formation is likely to be vigorous. As the characteristic frequency of the particle decreases, so does the speed at which the gas caps form. For example, for a sound wave frequency of 30 MHz, gas cap formation is high for particles having a size of 0.984 µm (2.16 MHz) but sluggish for particles having a size of 0.245 µm (34 MHz).

In step 200, the particles are subjected to a cavitation field in order to separate gas caps 60 and 80 from particle 50 to form bubbles 90 and 95 respectively. The cavitation field generally comprises a low frequency but high tensile pressure acoustic signal. When the tensile pressure on the gas cap overcomes the surface tension resistance along the perimeter of contact, fracture occurs. The peak negative pressure amplitude which causes this fracture is the cavitation threshold. When fracturing occurs, gas caps 60 and 80 break away from particle 50 to form bubbles 90 and 95 respectively. The high frequency field alone, however, is insufficient to create a high enough tensile pressure to cause the fracturing and therefore a high tensile pressure acoustic signal of the cavitation field may be employed.

Although gas caps 60, 80 are not perfect bubbles, because only minor differences in analysis exist between partial bubbles and bubbles, gas caps 60, 80 may be analyzed as bubbles. Every bubble has a radius at which the forces tending to expand the bubble overcome the forces trying to collapse the bubble. At that radius, known as the critical radius, the bubble experiences unbounded increase in size until it fractures. The Blake threshold is the acoustic pressure amplitude that causes the bubble radius to expand beyond the critical radius. The equation for the Blake threshold is given below:

$$R_c = \frac{4}{3} \frac{\sigma}{p_v - p_{lc}} \quad (1)$$

where $R_c$ is the critical radius, $\sigma$ is the surface tension of the water, $p_v$ is the pressure of the vapor in the bubble, and $p_{lc}$ is the acoustic pressure of the surrounding liquid. For example, for particles having a diameter of 0.984 µm, 0.481 µm, and 0.245 µm, the Blake thresholds are 1.96, 3.1 and 5.3 bar peak negative, respectively. Therefore, setting aside the fact that a high frequency acoustic signal does not afford enough time for significant bubble growth, the maximum pressure amplitude available in the high frequency acoustic signal used in step 100 of about 0.5 bar peak negative is well below the Blake threshold value necessary to cause unbounded growth in the gas caps. Therefore, the high frequency acoustic signal only pre-processes the particles for cavitation by engendering the formation of gas caps. The high frequency signal is not able to wrench off the gas caps because the gas caps do not grow to a size large enough for the low pressure of the high frequency signal to overcome the critical radius of the gas caps. Therefore, a cavitation field is used to focus a stronger tensile pressure toward the particles to cause the gas caps to reach the critical radius and thus for bubbles to separate at threshold values in step 200.

Figure 2C:
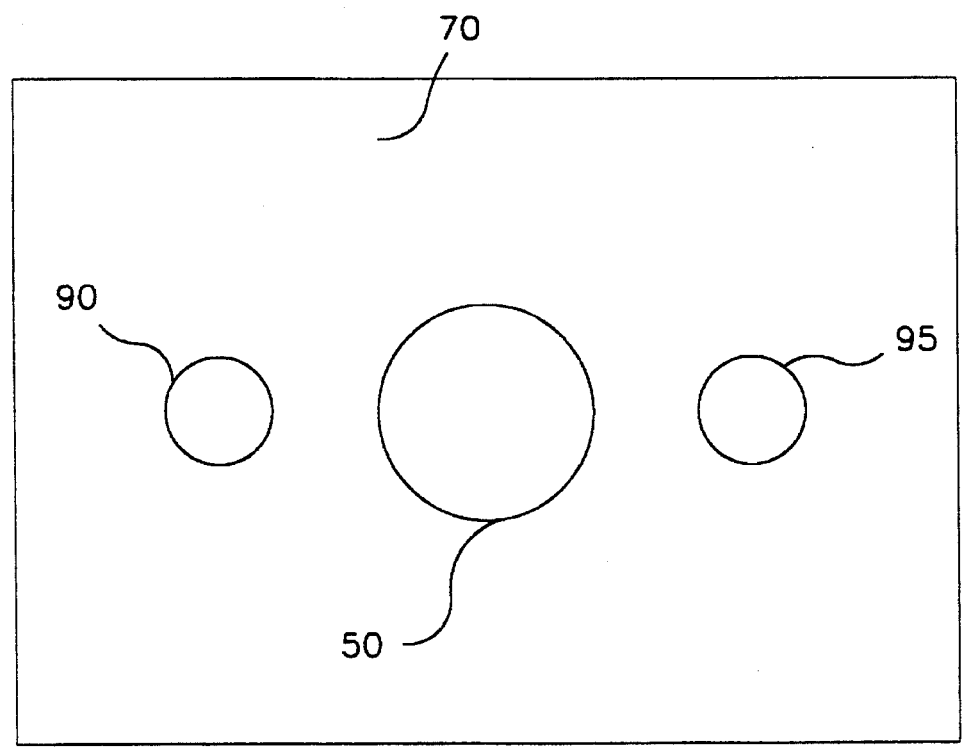
FIG. 2(c) depicts a schematic representation of a particle and two bubbles in a liquid produced through cavitation.

Referring to FIG. 2(c), when the cavitation field creates enough tensile pressure to overcome the surface tension on the particle, bubbles 90 and 95 separate from particle 50 in liquid 70. These bubbles, like any other component, reflect sound waves and create an echo which may be detected in step 300. The very presence of the bubbles is enough to detect particles based upon scattered sound. The acoustic signature of the bubbles is about 60 dB greater than the acoustic signature of the particles and thus detection of the acoustic signature due to sound wave echo becomes possible. Detection of an acoustic signature, as in step 300, is known. For example, an active transducer may be used. The transducer may be connected to receive acoustic signals which may then be displayed on an oscilloscope. Detection of a spike well beyond a noise level in the acoustic signal received would indicate the presence of (a) bubble(s). Size and shape analysis of bubbles using acoustic signatures is also well known.

By reducing the threshold level for cavitation, the resulting cavitation may be produced in a manner which is non erosive soft cavitation. Therefore, the cavitation produced does not damage the pipes and containers in which the liquid is stored. The present invention is thus suitable for in-line use because it does not harm the piping or container through which the liquid passes.

Figure 3:
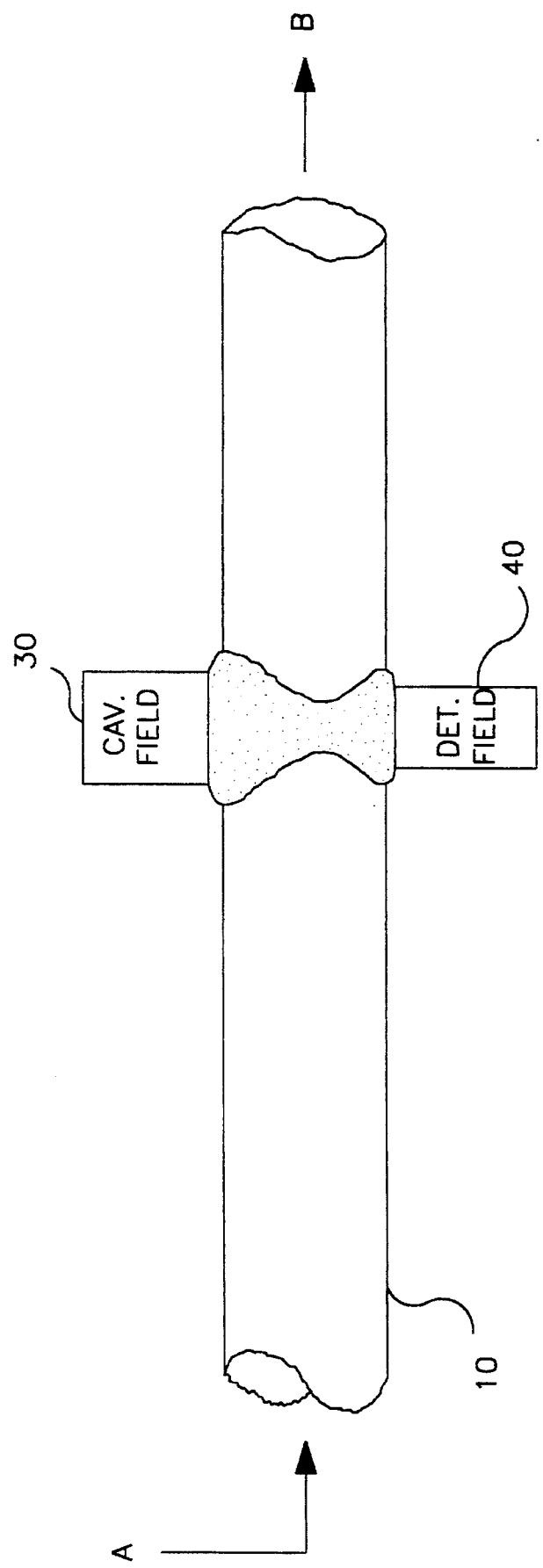
FIG. 3 depicts a schematic representation of an apparatus for detection of particles in liquids using acoustic scattering and cavitation.

Referring to FIG. 3, a schematic representation of an apparatus for the detection of particles in liquids is depicted. A liquid to be tested may flow through a pipe 10 in a direction from point A to point B. The liquid flows through the junction of a cavitation field 30 and a detection field 40. The liquid may then flow out of pipe 10 in the direction of B.

Pipe 10 may be any type of pipe whether transparent or opaque. Further, pipe 10 may be cylindrical or any other shape through which a liquid may flow. Further, the liquid may be contained in any other type of container and need not be flowing.

Detector field 40 may be an active acoustic transducer. An active acoustic transducer generates a weak, high frequency auxiliary field which coaxes the particles toward cavitation prior to passage through cavitation field 30. Detector field 40 may generate an auxiliary field operating at 30 MHz and 0.5 bar peak negative, for example. Detector field 40 may be generated by, for example, a focused 30 MHz active acoustic transducer used in a pulse-echo mode. Other focused, high frequency, low pressure signals may also be used. An active transducer such as a PZT, PZT-5 or PVDF may be used to generate the acoustic signal. Active transducers made by manufacturers such as Harrisonics, EBL or Panametrics may be used, for example.

Preferably, cavitation field 30 and detection field 40 are confocused. Preferably, both the cavitation pulse and the high frequency acoustic signal arrive simultaneously at the common focus, the region of cavitation. Cavitation field 30 is preferably a primary pulsed focused acoustic field of high intensity. Cavitation field 30 may be produced by a focused PZT-8, 0.75 MHz transducer driven in pulse mode. The pulse mode may operate with a duty cycle of about one per cent, for example. Other duty cycles may also be used. The focused PZT-8 may operate at a pressure amplitude about 30 times greater than the weak auxiliary field, or about 15 bar peak negative. Higher bar peak negative, such as 22 bar peak negative, fields may also be generated by the focused PZT-8. Preferably, the pressure amplitude of cavitation field 30 is about 30 times greater than the pressure amplitude of the auxiliary field. Focused systems have the advantage that the zone of cavitation is localized within the bulk of the liquid, away from the walls of the container and the rough transducer face. Also, a LZT-1 focused transducer may be used.

Detection field 40 operates as any other type of active transducer which transmits sound waves and receives the resulting echoes. The echoes received from the bubbles provide the necessary particulate detection, because as discussed before, if a liquid has no particulate, cavitation is likely not going to occur. For detection purposes, a passive detector may be additionally or alternatively used. For example, an unfocused, untuned 1 MHz transducer may be used as a passive detector.

Therefore the present invention has provided a system whereby particulate in liquids may be detected using acoustic scattering techniques. The present invention also provides a system which detects particulate through use of a fully in-line, robust and non-invasive method of monitoring even submicron particulate presence in clean liquid systems.

EXAMPLE 1

This example shows the effects of a high frequency acoustic signal on cavitation. A test chamber was filled with clean water (distilled, deionized and extensively filtered). A PZT-8, 0.75 MHz focused cavitation transducer operated in pulse mode with a duty cycle of about 1% was used to generate a cavitation field. A first unfocused, untuned 1 MHz transducer was used as a passive device. A second active transducer was a focused 30 MHz transducer used in pulse-echo mode at a pressure of about 0.5 bar peak negative. The pressure of the cavitation transducer was varied to determine the threshold for a clean liquid and a liquid containing particles. For the clean liquid, even when placed under the pressure from a cavitation transducer driven at its peak output of 22 bar peak negative, no cavitation was observed. Further, when monodispersed, spherical, smooth polystyrene latex microparticles of 0.984 µm mean diameter, suspended in clean water were irradiated with short acoustic pulses from the active transducer, cavitation thresholds indicated by the passive detector were around 15 bar peak negative. When the active transducer was activated to generate a high frequency acoustic signal which induced gas caps to form on the particles before cavitation, cavitation thresholds were measured at 5 bar peak negative. The passive transducer detected thresholds of 7 bar peak negative while the active transducer was operating. The difference of 7 bar peak negative detected by the passive transducer between when the active transducer was inactive and when the active transducer was active is not wholly attributable to the active transducer itself which was only operating at 0.5 bar peak negative. The gas cap formation induced by the active transducer generation of a high frequency acoustic signal effected the cavitation threshold.

Although the surfaces of the polystyrene latex particles used were measured to be smooth down to 500 Å, nanoscale gas pockets may still exist on the surface of the particles. If a single nano-gas-dot of diameter 50 nm were to cavitate alone in the tensile environment of the cavitation transducer, the estimated threshold would be around 60 bar peak negative. Consequently, the observed lower thresholds in the presence of the active detector field are possible if the nano-gas-dots aggregate to form sufficiently larger gas patches or gas caps. In water, for example, the wavelengths at 30 MHz and 0.75 MHz are 50 μm and 2 mm, respectively, while the largest particles used in the experiment are less than 1 μm in diameter. In these circumstances, a particle feels essentially a uniform pressure over its surface. Also, in the focal zone of a focused transducer the waves may be assumed to be nearly planar. In water, the active detector operating at 30 MHz at a modest pressure level setting of 0.5 bar peak negative may give rise to a particle (fluid parcel) acceleration of about $6.47 \times 10^6$ m/s$^2$, or equivalently $6.5 \times 10^5$ g's. At any given point a particle denser than water will inertially lag the acceleration, while a less dense particle will move in the direction of acceleration. The density of polystyrene spheres is 1.05 g/cc, which is reasonably matched with the density of water. Air density, on the other hand is about $1.2 \times 10^{-3}$ g/cc. Coupled with high acceleration fields, this density contrast, a factor of 830, will enhance the kinetic buoyancy and urge the nano-gas-dots towards the fore and aft regions on the particle where they may agglomerate and form gas caps. Gas caps may be visualized as lens-like regions located at the extremities of an oscillating (to and from) spherical particle. A cavitation event may then occur when the force due to surface tension on the perimeter of the gas cap is overcome by the tensile forces effective on the gas region.

In the case of the polystyrene spheres of mean diameter 0.984 μm, the measured passive detector threshold was 7 bar peak negative in the presence of the active detector field. The surface tension (0.073 N/m) force acting on the perimeter of a circle of diameter 0.984 μm may be overcome by a tensile force due to a pressure of just 3 bar peak negative acting on the corresponding projected area, assuming a gas cap the same size as the diameter of the particle. In reality, the gas cap is likely to be smaller than the particle dimensions. This would, as observed, invariably give rise to thresholds higher than the lower limit corresponding to a gas cap as large as the particle diameter, or a bubble exactly encapsulating the particle. For a single nano-gas-dot of size 50 nm, to cavitate alone in the tensile environment of the cavitation transducer, the estimated threshold would be around 60 bar peak negative. Gas collection in the form of gas caps due to kinetic buoyancy explains cavitation promoted by even smooth particles and the reduced thresholds present during the activation of the active detector field.

EXAMPLE 2

Figure 4:
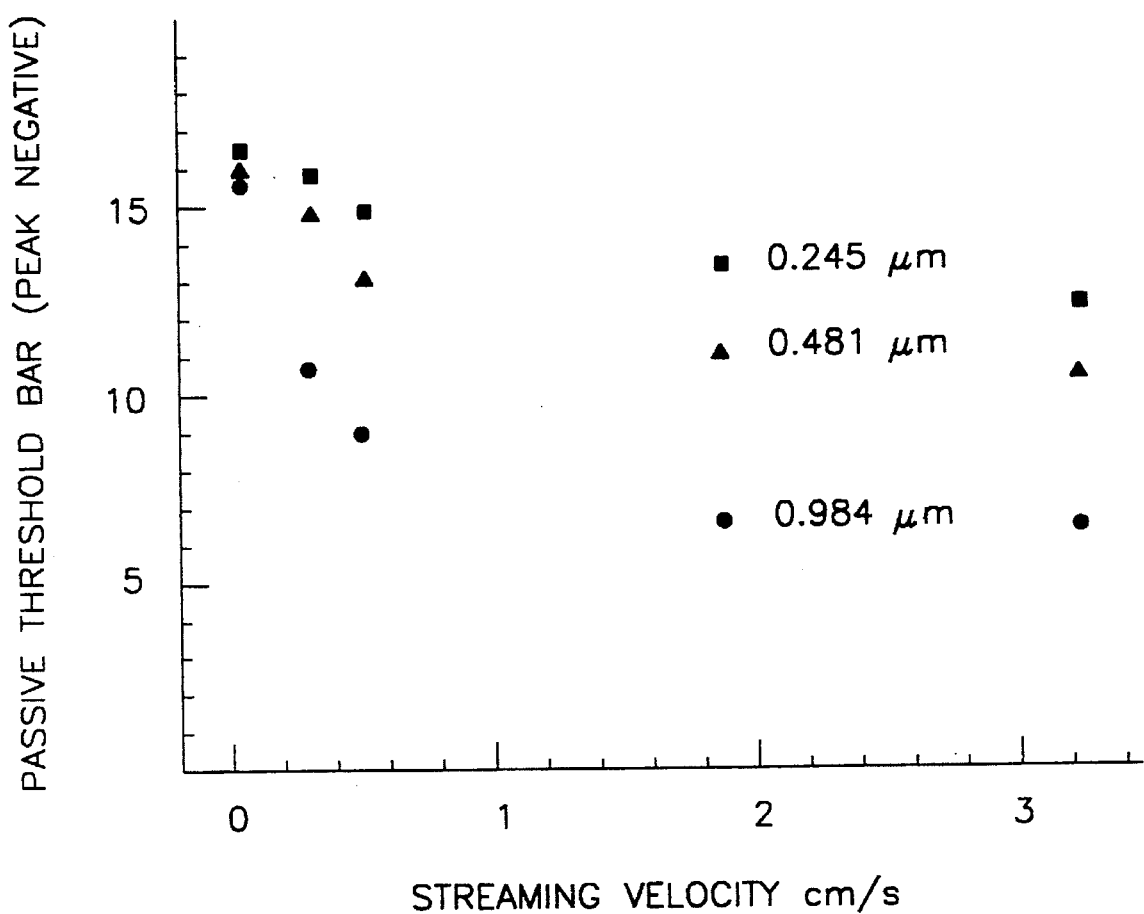
FIG. 4 depicts a graph of threshold values detected for varying sizes of particles and varying usage of an active transducer.

This example shows cavitation threshold reduction due to the use of the active transducer producing a high frequency acoustic signal. FIG. 4 depicts how passive thresholds vary as a function of the streaming velocities for different particle sizes. Streaming velocity is a second order acoustic effect manifested by a hydrodynamic flow caused by an acoustic field and varies typically as the square of the frequency, intensity and attenuation. Being a high frequency focused device, an active detector causes acoustic streaming and convects particles in the focal zone of the main cavitation transducer. Here, streaming velocity is used as a convenient abscissa to represent the different settings of the active detector field. The magnitudes of the streaming velocities are small and streaming is not expected to affect the physics of cavitation. The streaming velocity depends on the setting of the active detector and stronger active detector fields give rise to stronger streaming; the maximum streaming may be set to 3.25 cm/s. Zero on the abscissa corresponds to zero active detector field; active detector switched off.

Essentially, monodispersed, polystyrene particles of three different sizes, having mean diameters of 0.245 μm (represented by the square), 0.481 μm (represented by the triangle), and 0.984 μm (represented by the circle) were tested. Particle number density was maintained the same at $1.91 \times 10^8$ particles/cc. Dissolved air saturation in the test cell was held to around 70%. Increasing streaming velocity corresponds to increasing active detector usage. The cavitation field used was a cavitation transducer operating at a 10 μs pulse and a 1 kHz PRF signal confocal setting.

When the active detector is switched off, it does not participate in the cavitation process; the thresholds are solely due to the main cavitation field. The observed passive thresholds are around 15 bar peak negative with the smaller particles giving a slightly greater value. If the main cavitation transducer were to act alone, in order to give rise to the acceleration levels as high as those due to the active detector (set to yield a streaming of 3.25 cm/s), i.e., set to generate an acoustic signal at 30 MHz and a pressure amplitude of 0.5 bar peak negative. At similar acceleration levels, it is reasonable to expect that the particles acting alone to produce comparable levels of acceleration, the cavitation event may take place readily as the main cavitation field is already stronger than the threshold values when the active detector field is present. At the intermediate levels of the active detector settings, the observed passive detector thresholds assume intermediate values. With only the main cavitation field present, the thresholds for the particles are essentially the same, around 15 bar peak negative, with the smaller particles yielding a slightly higher threshold than the larger particles. The effect of particle size becomes more pronounced at the stronger active detector field (higher streaming velocities). As FIG. 4 indicates, therefore, the active detector generating a high frequency acoustic signal reduces the threshold level for cavitation.

Although a detailed description of the invention has been provided, it should be understood that the scope of the invention is not to be limited thereby, but is to be determined by the claims which follow. Various modifications and alternatives will be readily apparent to one of ordinary skill in the art.

I claim:

1. A method for the detection of particles in a liquid comprising the steps of:

nucleating cavitation from each particle within the liquid by simultaneous application of a high frequency acoustic field and a low frequency, high tensile pressure pulsed cavitation field said step of nucleating cavitation comprising:

inducing gas caps to form on said particles; and, separating said gas caps from said particles to form bubbles in said liquid; and detecting an acoustic signature which comprises a reflection of said high frequency acoustic field or said low frequency, high tensile pressure pulsed cavitation filled off of said bubbles, whereby said acoustic signature indicates that the particles are present in the liquid.

2. The method of claim 1 further comprising the step of generating the high frequency acoustic field by providing an active transducer in said liquid focused at said particles.

3. The method of claim 1 further comprising the step of generating the high frequency acoustic field by providing an active transducer generating an acoustic field having a frequency of about 30 MHz and a tensile pressure of about 0.5 bar peak negative in said liquid.

4. The method of claim 1 further comprising the step of generating the low frequency, high tensile pressure pulsed cavitation field by providing a transducer generating a cavitation field having a frequency of about 0.75 MHz.

5. The method of claim 1 further comprising the steps of:

generating the high frequency acoustic field by providing an active transducer in said liquid;

generating the low frequency, high tensile pressure pulsed cavitation field by providing a high pressure transducer in said liquid; and confocusing said active transducer and said high pressure transducer.

6. An apparatus for detecting particles in a liquid comprising:

means for nucleating cavitation from each particle within the liquid by simultaneous application of a high frequency acoustic field and a low frequency, high tensile pressure pulsed cavitation field; and means for detecting an acoustic signature received as an echo from said bubbles, whereby said acoustic signature indicates that the particles are present in the liquid.

7. The apparatus of claim 6 wherein said means for nucleating cavitation comprises an active transducer which generates the high frequency acoustic field in said liquid.

8. The apparatus of claim 6 wherein said means for nucleating cavitation comprises an active transducer which generates the high frequency acoustic field at a frequency of about 30 MHZ and a tensile pressure of about 0.5 bar peak negative in said liquid.

9. The apparatus of claim 6 wherein said means for nucleating cavitation comprises a transducer generating a pulsed low frequency, high tensile pressure cavitation field at a frequency of about 0.75 MHz.

10. The apparatus of claim 6 wherein said means for nucleating cavitation comprises:

an active transducer generating the high frequency acoustic field in said liquid;

a high pressure transducer generating a pulsed cavitation field in said liquid; and wherein said active transducer and said high pressure transducer are confocused.

11. A method for the detection of particles in a liquid comprising the steps of:

reducing a threshold pressure at which cavitation is induced within the liquid, said step of reducing the threshold pressure comprising simultaneous application of a high frequency acoustic field and a low frequency, high tensile pressure pulsed cavitation field to the liquid;

generating cavitation in the liquid at said reduced threshold pressure through use of said low frequency, high tensile pressure pulsed cavitation field; and detecting acoustic echoes received from bubbles which result from said cavitation;

whereby said echoes indicate that the particles are present in the liquid.

12. A method for the detection of particles in a liquid comprising the steps of:

reducing a threshold pressure at which cavitation is induced in the liquid by generating a high frequency, low pressure acoustic field to induce gas caps to form and grow on said particles in said liquid, each gas cap being held in contact with a particle by surface tension;

generating a low frequency, high tensile pressure pulsed cavitation field to separate said gas caps from said particles to form bubbles in said liquid, said high pressure being sufficient to overcome the surface tension holding each gas cap in contact with a particle and being about equal to the reduced threshold pressure; and detecting an acoustic signature which comprises a reflection of said high frequency, low pressure acoustic field off of said bubbles, whereby said acoustic signature indicates that the particles are present in the liquid.

13. The method of claim 12 further comprising the step of confocusing said high frequency, low pressure acoustic field and said low frequency, high tensile pressure pulsed cavitation field.

14. An apparatus for the detection of particles in a liquid comprising:

means for reducing a threshold pressure at which cavitation is induced within the liquid by generating a high frequency, low pressure acoustic field to induce gas caps to form and grow on said particles in said liquid, each gas cap being held in contact with a particle by surface tension;

means for generating a pulsed low frequency, high tensile pressure cavitation field to separate said gas caps from said particles to form bubbles in said liquid, said cavitation field having a pressure sufficient to overcome the surface tension holding each gas cap in contact with a particle and being about equal to the reduced threshold pressure; and means for detecting an acoustic signature which comprises a reflection of said high frequency, low pressure acoustic field off of said bubbles, whereby said acoustic signature indicates that the particles are present in the liquid.

15. The apparatus of claim 14 wherein said means for generating a high frequency, low pressure acoustic field and said means for generating a pulsed low frequency, high tensile pressure cavitation field are confocused.

16. A method for the detection of particles in a liquid comprising the steps of:

generating a high frequency, low pressure acoustic field to induce gas caps to form and grow on said particles;

generating a low frequency, high tensile pressure pulsed cavitation field to separate said gas caps from said particles to form bubbles in said liquid; and detecting an acoustic signature which comprises a reflection of said high frequency, low pressure acoustic field off of said bubbles, whereby said acoustic signature indicates that the particles are present in the liquid.

17. The method of claim 16 wherein the low frequency, high tensile pressure pulsed cavitation field has a duty cycle of about 1 percent.

18. The method of claim 16 wherein the step of generating a high frequency, low tensile pressure acoustic field comprises operating a high frequency transducer in pulse echo mode.

19. The method of claim 1 wherein the low frequency, high tensile pressure pulsed cavitation field has a duty cycle of about 1 percent.

20. The apparatus of claim 6 wherein the low frequency, high tensile pressure pulsed cavitation field has a duty cycle of about 1 percent.

21. The method of claim 11 wherein the low frequency, high tensile pressure pulsed cavitation field has a duty cycle of about 1 percent.

22. The method of claim 12 wherein the low frequency, high tensile pressure pulsed cavitation field has a duty cycle of about 1 percent.

23. The apparatus of claim 14 wherein the low frequency, high tensile pressure pulsed cavitation field has a duty cycle of about 1 percent.

* * * * *